United States Patent [19]
Goto et al.

[11] Patent Number: 4,735,215
[45] Date of Patent: Apr. 5, 1988

[54] SOFT TISSUE BIOPSY INSTRUMENT

[76] Inventors: David S. Goto, 2240 Lee St., Lakewood, Colo. 80215; Gary Brunner, 6158 Owens St., Arvada, Colo. 80004

[21] Appl. No.: 465

[22] Filed: Jan. 5, 1987

[51] Int. Cl.⁴ .............................................. A61B 10/00
[52] U.S. Cl. .................................................... 128/754
[58] Field of Search ............... 128/753, 754, 751, 305, 128/354, 321

[56] References Cited

U.S. PATENT DOCUMENTS 2,496,111  1/1950  Turkel .................. 128/754

FOREIGN PATENT DOCUMENTS 141108  4/1980  German Democratic Rep. ..................... 128/754
387704  9/1973  U.S.S.R. ................. 128/754

Primary Examiner—Michael H. Thaler
Attorney, Agent, or Firm—Morris Fidelman; Franklin D. Wolffe

[57] ABSTRACT

A trocar type biopsy instrument characterized by:
(a) structure for locking the cannula and stylet of the instrument together so as to allow these components to penetrate soft body jointly as a unitary whole;
(b) structure for retracting the cannula rearward along the stylet far enough to expose the specimen notch, and for returning the cannula along the stylet to its original advanced position covering the specimen notch;
(c) removable stylet retaining structure so that the stylet may be removed while the cannula remains locked in its advanced position.

The instrument of the present invention facilitates the manipulative efforts required for performing soft tissue biopsy procedures.

3 Claims, 2 Drawing Sheets

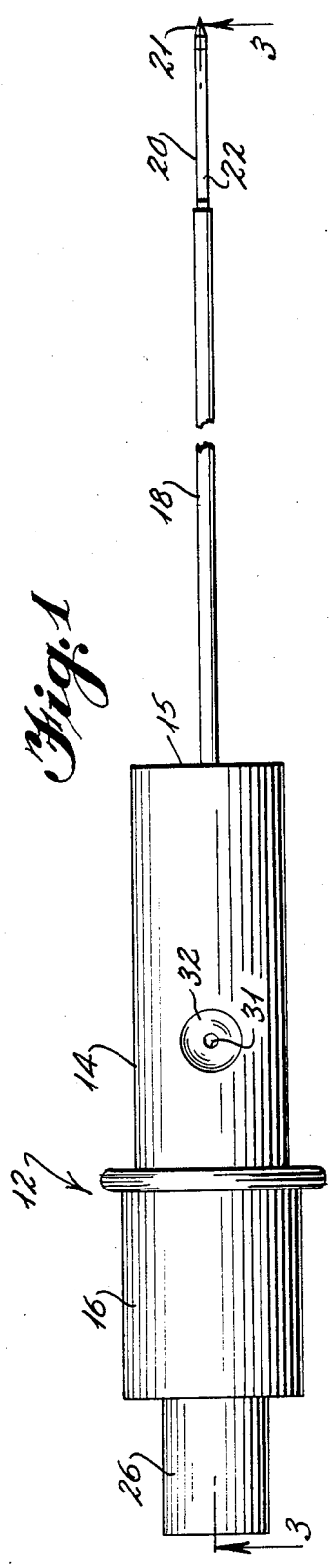
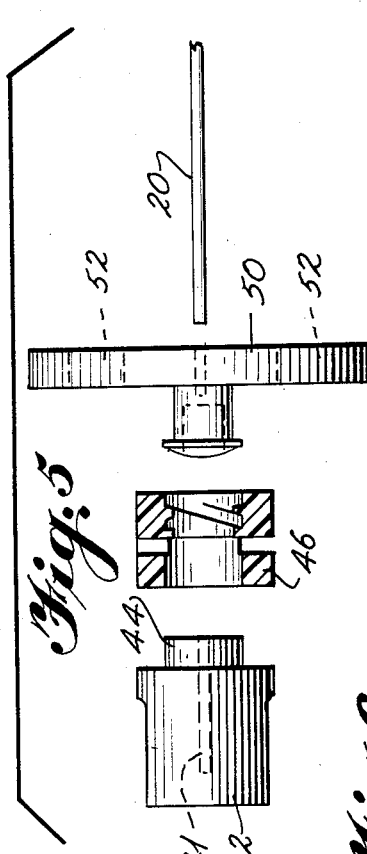
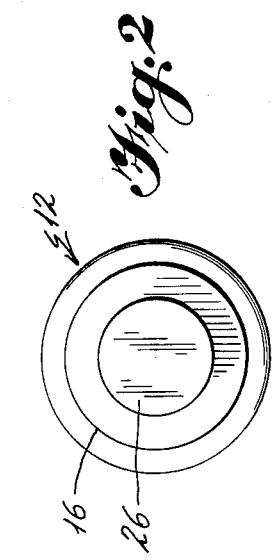
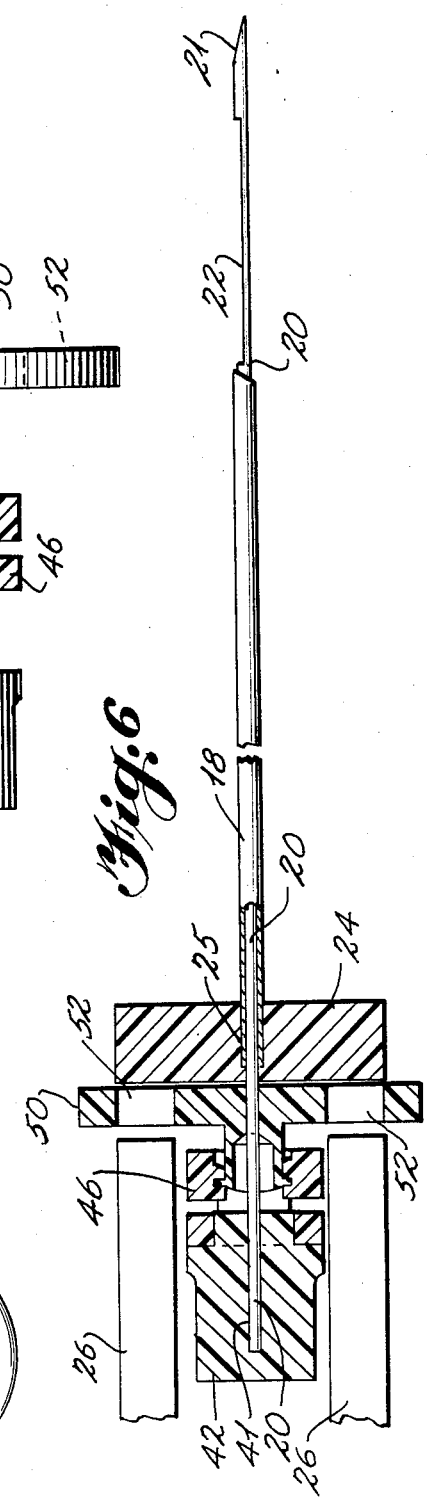

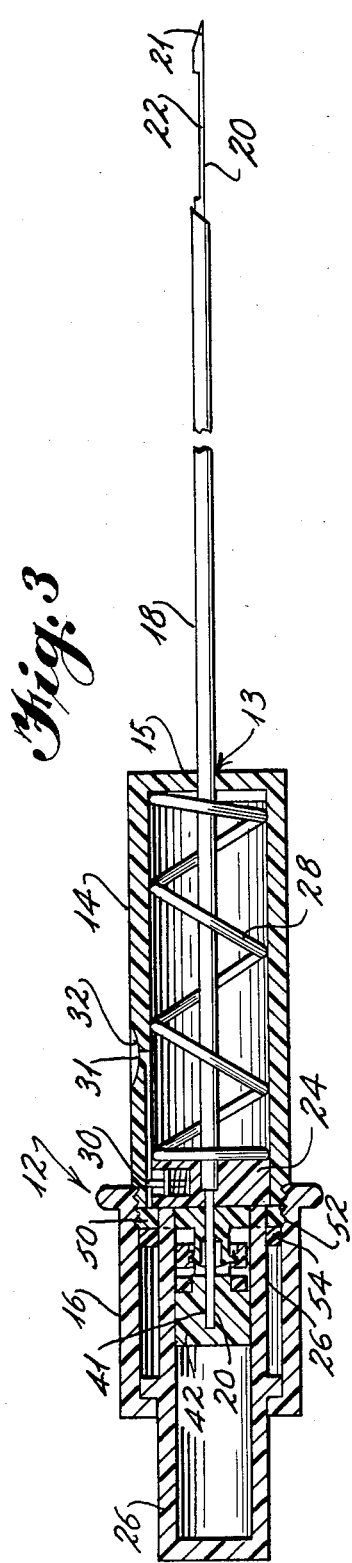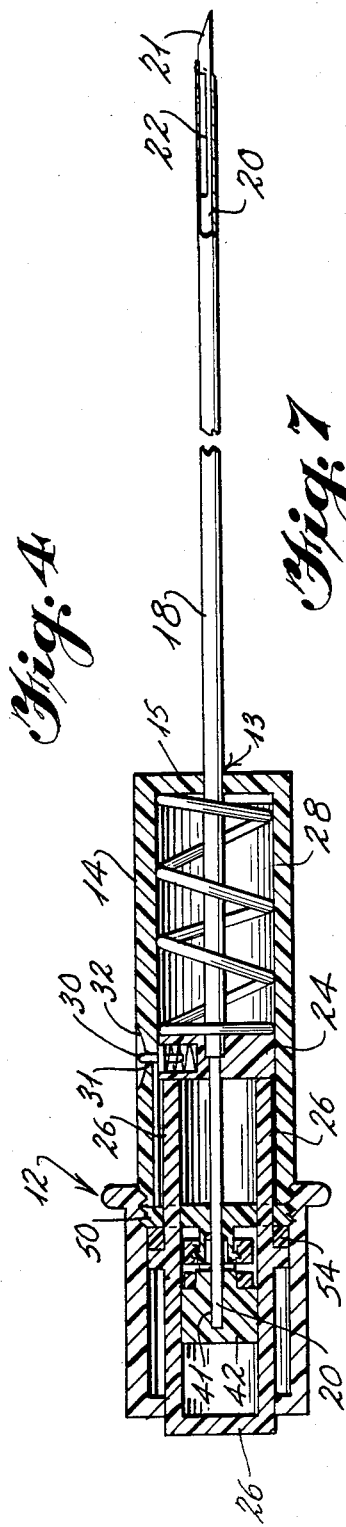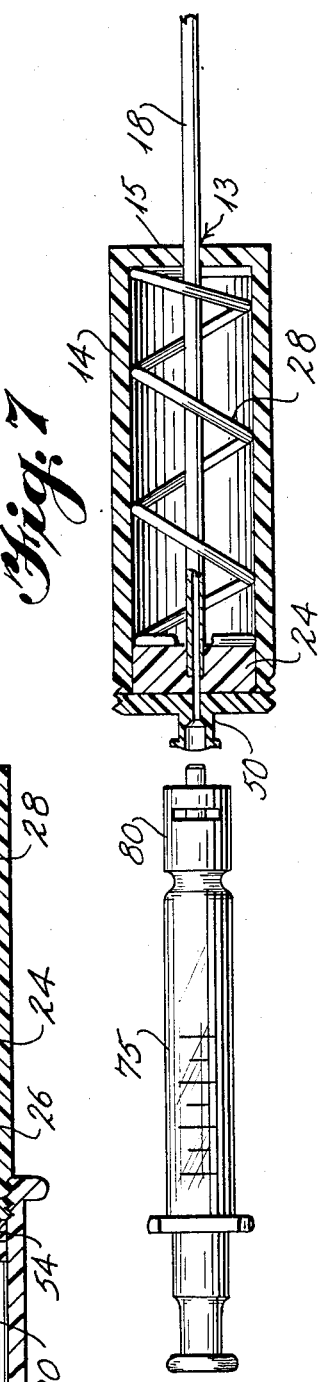

SOFT TISSUE BIOPSY INSTRUMENT

The present invention relates to the performance of biopsies on living tissue, animal or human, and particularly to an improved surgical instrument for performing such biopsy procedures. As used herein, the term "biopsy" refers to the collection of a soft tissue specimen for purposes of examination, disease identification and diagnosis.

BACKGROUND OF THE INVENTION

Typically, biopsy procedures are performed to obtain specimens of tissue from an internal organ of suspect for detection of disease conditions, such as cancer, and are of particular utility in determining the extent of the spread of the disease prior to the performance of surgery or therapy. Where, for instance, an abnormality is suspected in soft tissue organs such as the liver, spleen, pancreas, glands, etc., or where a growth has been located and it is desired to determine the nature and extent of the growth, a biopsy may be performed in order to obtain tissue specimens for laboratory examination. In general, biopsy procedures are preferred over the difficulty and trauma of exploratory surgery.

An instrument, commonly referred to as a trocar, employed for obtaining tissue core specimens comprises a small diameter long tubular cannula and a long thin sharp-tipped stylet located inside the cannula and movable relative to the cannula. The stylet may be provided with a specimen notch on its periphery near proximal tip of the stylet. The proximal end of the cannula may be sharpened.

The trocar is inserted through a small incision or puncture made in the skin and driven into the body until its sharpened end enters the organ of suspect. During this insertion stage of the procedure the stylet is positioned within the cannula so that no more than the sharp tip of the stylet is exposed; the specimen notch is covered by the cannula. Once the instrument has been positioned at the site for the biopsy, the cannula is retracted along the stylet enough to expose the specimen notch in the stylet. Soft body tissues will then prolapse around the newly exposed portion of the stylet and into the specimen notch, whereupon the cannula can then be advanced along the stylet to cover the specimen notch once again. This forward movement of the cannula cuts out a specimen of the prolapsed tissue, which specimen becomes retained in the specimen notch of the stylet. With the cannula still concealing the specimen notch, the trocar may then be withdrawn carefully from the target site. Thereafter, the cannula is once again retracted to expose the specimen notch of the stylet, creating access to the tissue specimen sample contained therein. If the physician desires to obtain multiple specimens from the same site, the cannula may be maintained stationary in its advanced position at the biopsy site while the stylet is withdrawn through the distal end of the cannula. This removal also exposes the specimen notch, so that the specimen may be removed therefrom. The same or a like stylet can then be inserted into the cannula, whereupon the above-described specimen collecting and removing procedure may be repeated to obtain the additional specimens desired.

Several problems can arise during employment of known cannula and stylet type trocar devices for tissue biopsy procedures. The known devices are often difficult for the surgeon to manipulate, especially when the target site is deep within the body, and the relatively long biopsy device must be guided and located inside of the body by radiographic imaging. Further, even though some trocar devices are provided with ring, bar or loop type grip means, it is usually necessary for the surgeon to employ both hands to manipulate the trocar, and often the surgeon requires assistance from another person to perform the cutting operation that obtains the tissue specimen. Difficulty in manipulating the cannula while maintaining the stylet in an exact position at the target site is further compounded in the instance of trocar devices which incorporate separate obturator means for covering the stylet notch, since such is an additional element which must be manipulated during the biopsy.

In all biopsies, it is desirable to perform the cutting procedure quickly in order to prevent the prolapsed tissue in the specimen notch from being displaced outwardly during advance of the cannula end along the stylet. Slow movement by the cannula might result in insufficient specimen being obtained. Manipulation problems arise because the trocar structure must provide for the cannula and stylet to be movable together as a unit, and to be movable separately relative to one another. While the cannula is being retracted and then advanced along the stylet, the stylet might inadvertently move also, which movement could result in an unsuccessful biopsy procedure.

Manipulation problems can arise when it is desired to obtain multiple tissue specimens from either the same target site, or from several depths among the same puncture tract. As has been pointed out above, after a specimen has been secured within the specimen notch, the stylet will be taken out through the distal end of the cannula to provide access to the tissue specimen reposing therein yet leave the cannula in place. Then the same or a like stylet must be advanced completely through the cannula. Because the stylet is quite thin and often is of considerable length, care must be exercised when retracting and advancing the stylet (within the cannula) in order to prevent bending of the stylet. A bent stylet might bind in the cannula. The stylet is supported over its entire length only when fully inserted within the cannula. This tends to make insertion and advance of the stylet in the cannula, during multiple biopsy procedure, a carefully done two-handed procedure. Complete retraction and reinsertion of the stylet becomes relatively time consuming and undesirable patient trauma might occur because the biopsy procedure cannot be performed quickly.

It is, therefore, an object of the present invention to provide an improved soft tissue biopsy instrument of the cannula and stylet type which overcomes shortcomings of prior art trocar devices, is reliable in operation and may be used with advantageous facility, and which is of simple construction and relatively inexpensive to manufacture.

SUMMARY OF THE INVENTION

The soft tissue biopsy instrument of the present invention is a trocar of the cannula and stylet type wherein a small diameter tubular cannula has disposed therein a longer needle-like stylet. The proximal ends of both the stylet and cannula of the present instrument are beveled relative to their longitudinal axes and are sharpened to facilitate puncturing soft tissues and cutting the biopsy tissue specimen. A longitudinal specimen notch is provided in the outer surface of the stylet proximate the stylet tip.

The structure of the present invention provides a housing for the rear portions of the cannula and stylet within which are present:

(a) means for locking the cannula and stylet together so as to allow these components to penetrate soft body jointly as a unitary whole;

(b) means for retracting the cannula rearward along the stylet far enough to expose the specimen notch, and for returning the cannula along the stylet to its original advanced position covering the specimen notch;

(c) removable stylet retaining means so that the stylet may be removed while the cannula remains locked in its advanced position.

The instrument of the present invention facilitates the manipulative efforts required for performing soft tissue biopsy procedures. The surgeon is freed from need to control retraction of the cannula, and retains full control over the cutting advancing motion of the cannula along the stylet. The surgeon can readily retain the stylet steady at the target site. The trocar of this invention permits a facile removal and replacement of the stylet in the event multiple specimens are sought. The same or a like stylet may easily and quickly be repositioned within the cannula.

DETAILED DESCRIPTION OF THE INVENTION

For further understanding of the invention, reference is made to the attached drawing wherein:

FIG. 1 is a side elevational view of the trocar of this invention;

FIG. 2 is an end view of the trocar.

FIG. 3 is a cross-section taken along lines 3—3 of FIG. 1.

FIG. 4 is a cross-section taken along lines 3—3 of FIG. 1 with the cannula in extended position.

FIG. 5 is a section of the stylet retaining members.

FIG. 6 is a partial section along lines 3—3 of FIG. 1 with parts broken away illustrating the trocar with the stylet extended.

FIG. 7 is a partial cross-section diagrammatically illustrating how a syringe may be coupled to the cannula.

Referring now to the drawing, and in particular to FIG. 1, it may be seen that the trocar comprises a housing 12 formed from two components, e.g., housing halves, 14 and 16, secured together. Extending axially forward of housing 12 are the concentrically disposed cannula 18 and stylet 20. As best may be seen in FIG. 6, a specimen notch 22 adjacent the tip 21 of the stylet 20 is normally covered by the cannula 18 when stylet and cannula are locked together for tissue penetration purpose, but becomes exposed upon retraction of cannula 18. When cannula and stylet are locked for penetration, the stylet tip 21 extends a modest distance forward of the cannula terminus, typically 3 or 4 mm, and appropriately the proximate end 23 of specimen notch 22 is correspondingly 4 or 5 mm distally of stylet tip 21. Exemplary lengths for the stylet (forward from housing 12) are 3½", 6" and 8". The extended and retracted positions for cannula 18 are illustrated by FIGS. 3 and 4 respectively.

Inside housing 12, the cannula 18 is secured centrally of housing 12 to a movable hub 24, which member 24 constitutes a plunger riding the inside wall of housing half 14 impelled by movement of cap 26. Spring 28 resists forward movement by cap 26 and hub 24 and generates retraction movement, as is illustrated by FIGS. 3 and 4. A spring biased detent 30 set in the periphery of hub 24 engages in a central aperture 31 of the circular groove 32 on the side wall of the front housing half 14 to lock hub 24 and cannula 18 in their forward rest position. Then, movement of detent 30 radially inward releases the hub 24 allowing spring 28 to push the hub and cannula rearward to their retracted rest position, see FIG. 3. A driver cap 26 extending distally out from rear housing half 16 bears against the hub 24. Thumb pressure against cap 26 causes cap 26 and hub 24, and cannula 18, to move forward as a unitary whole. The spring force of spring 28 causes cannula and hub to retract.

Through the presence of detent 30 in aperture 31, the cannula and stylet are locked together and move as a unit while the trocar is being inserted. Then, when detent 31 is depressed sufficient to clear the aperture 31 spring 28 causes hub 24 and cannula 18 to retract. Thus, no undesired added penetration of tissue takes place by virtue of any forward movement of the cannula. As may be seen in FIG. 3, retraction of cannula 18 along stylus 20 has exposed the notch 22 in stylus 20. Some of the soft tissue which collapses around stylus 20, enters notch 22. A subsequent advance of cannula 18 along stylus 20 traps (specimen) tissue in notch 22.

The concentricity of cannula 18 and stylet 20 along with location of the above-described latching mechanism for cannula 18 peripherally of the cannula makes feasible the already described movement of the cannula 18 relative to the stylet. The stylet can be moved relative to the cannula as well.

The cannula 18 slidably fits a central aperture 13 in the front face 15 of housing 14, and is affixed at periphery to the wall of a central aperture 25 of hub 24 (see FIG. 6). Also the spring 28 and the hub locking detents 30 are radially outward of the cannula. Thus, cannula 18 is secured within housing half 14 when locked in its forward rest position, but is free to move axially between its forward and its retracted position. Thus, stylet 20 occupies what otherwise would be an open axial space that extends from the proximate end of cannula 18 to the distal end thereof being clear of the cannula and the mechanism which advances and retracts the cannula. Appropriately, cap 26 is made hollow so that when cap 26 is pushed, advancing cannula 18 relative to housing 12, the distal end of the stationary stylet 20 is encompassed within the cap hollow, as may be seen in FIGS. 3 and 4. The stylet 20 is, of course, longer than the cannula 18.

As may be seen in FIGS. 4 and 5, the rear end of stylet 20 is mounted fixedly in a blind hole 41 of a stylet hub 42 and in turn stylet hub 42 is formed with a reduced diameter face 44 that interengages in a press and/or glued together fit with locking ring 46. The locking ring 46 interengages with mounting ring 50 through a Luer-locking mechanism (not fully illustrated). The mounting ring 50 is made integral with forward housing half 14 and serves to lock stylet 20 to the housing half 14, e.g., through the Luer-lock arrangement. The slots 52 in mounting ring 50 allow part of the cap 26 to reciprocate therethrough and move the cannula hub 24. The forward end of cap 26 is split into a multiplicity of lugs, e.g., four, the lugs being sized to pass through the slots 52 against cannula hub 24. FIG. 6 illustrates the relationship of the lugs on cap 26 to slots 52 of mounting ring 50. Since cannula 18 and stylus 20 are both locked to housing 12, they move as a unitary whole during penetration of the trocar into the body tissues.

Important to practice of this invention is capability to remove cap 26 and stylet hub 42. The housing halves 14 and 16 are separably threaded together. They may be separated when cannula 18 is locked to housing half 14 by detect 30 in its advanced position (covering specimen notch 22), as shown in FIG. 4 when cannula hub 24 is then well within housing half 14, or when cannula hub is in its retracted position, as shown in FIG. 3.

As can be appreciated from the drawing, cap 26 is free to rotate relative to rear housing half 16 so that when housing half 16 is being unthreaded (or threaded) cap 26 remains rotationally fixed to housing half 14. A retaining ring 54 holds cap 26 within housing half 16 so cap 26 and housing half 16 are withdrawn together.

Separating the housing halves 14, 16 and removing housing half 16 axially to the rear leaves the stylet hub 42 and locking ring 46 exposed. Stylet 20 can be withdrawn from cannula 18 by twisting and relasing the Luer-lock. A like stylet 20 can quickly and easily be inserted into the cannula 18 locking ring 46 secured to mounting ring 50 on housing half 14, after which cap 26 can be repositioned in the slots 52 of mounting ring 50 and the housing halves joined together. As has already been pointed out when housing half 16 is separated from housing half 14, the cap 26 remains with housing half 16. The retaining ring 54 provided to retain cap 26 in housing half 16 is recessed inside housing half 16 to provide a recess region wherein mounting ring 50 seats. The threaded connection between housing halves 14 and 16 illustrated herein could as well be the Luer-lock found on many medical devices, notably syringes.

The trocar of this invention is adapted for ease of use. Housing 12 can be gripped by the fingers of one or both hands for insertion of the needle and cannula as deeply into the body as required for the biopsy. To secure a tissue specimen, the surgeon can steady the housing 12 with the fingers of one hand while pressing detent 30 with the thumb of the other hand. When detent 30 is clear from aperture 31, the spring 28 causes retraction of cannula 18 to expose the stylet 20, collecting then a tissue specimen in notch 22. Thereafter the cap 26 is pressed forward, under the physician's control against spring 28, advancing cannula 18 to its fullest extent and engaging detent 30 in aperture 31. Whenever more than one biopsy specimen is wanted from the site, housing half 14 may be steadied by one hand, and housing half 16 twisted by the other hand. Then, housing half 16 is removed to expose the stylet for removal thereof. Given a second like stylet assembly at hand, stylet replacement may be done quickly, allowing a repeat specimen to be obtained promptly without moving the trocar.

A syringe can be coupled to housing half 14 should the physician desire to irrigate or medicate the tissues at the proximate end of cannula 18. FIG. 7 diagrammatically illustrates a syringe 75 coupled to housing half 14. The Luer-lock 80 on a standard syringe couples to locking ring 50. It may be noted that cannula hub 24 is in retracted position so as to create a well defined channel from the syringe 75 into cannula 18. Then expulsion of the (liquid) contents of syringe 75 sends the solution directly into cannula 18 to irrigate the body tissues at the proximate end of cannula 18.

No discussion is offered about the materials from which the trocar of this invention is found. Medical grade plastic materials (e.g., ABS plastic), capable of radiation sterilization are known in the art and the important metal components like the cannula and stylet are well known in the medical arts. Advantageously this entire assembly can be made as a disposable unit.

I claim:

1. A soft tissue biopsy instrument of the trocar type comprising:

a long sharpened cannula; a stylet longer than said cannula slidably enclosed within said cannula, from beyond the rear thereof, to at least the proximal tip end of the cannula, and a specimen notch on said stylet adjacent the proximate tip end thereof normally concealed by said cannula;

a housing encompassing the rear ends of said cannula and stylet wherein said cannula and stylet are independently mounted, said cannula and stylet being disposed axially of said housing;

means in said housing for mounting and shifting said cannula axially thereof inside said housing between a forward position whereat said cannula conceals said specimen notch and a retracted position whereat said specimen notch is exposed, said mounting and shifting means being spring biased toward the retracted position;

releasable means for retaining said cannula in place in forward position;

said housing being split into separable front and rear portions, the cannula mounting and shifting means and retaining means being disposed in the front portion of said housing;

a cap positioned at the rear of said housing movably mounted in the rear portion of said housing for movement axially of said cannula and bearing against the means for shifting said cannula, whereby finger pressure on said cap causes forward shifting of said cannula;

stylet mounting means removably securing said stylet to the front portion of said housing; and whereby said cannula and said stylet may be coaxially disposed with the cannula concealing said specimen notch and be inserted into body tissues as a unitary whole, then the cannula moved as aforesaid, and whereby the rear portion of the housing may be separated from the front portion and allow removal of said stylet while leaving the cannula in place.

2. A biopsy instrument as in claim 1 wherein said retaining means comprises a side wall aperture in the front portion of said housing and a spring biased detent in said mounting and shifting means for the cannula extendable into said aperture and then retaining said mounting and shifting means for said cannula in forward position.

3. A biopsy instrument as in claim 1 wherein said stylet mounting means comprises a stylet hub positioned in the rear portion of said housing and wherein said stylet is fixed, and locking means on said hub lockable to the front portion of said housing, whereby separation of the front and rear portions of said housing exposes the stylet hub and allow removal of stylet hub from the front portion of said housing and therewith said from said cannula through the rear thereof.

* * * * *